United States Patent
Jimenez et al.

(10) Patent No.: US 9,526,323 B2
(45) Date of Patent: Dec. 27, 2016

(54) TISSUE CLEANER AND ORAL CARE IMPLEMENT

(75) Inventors: Eduardo J. Jimenez, Manalapan, NJ (US); Robert Moskovich, East Brunswick, NJ (US); Andreas Wechsler, Austria (AT); Joachim Storz, Austria (AT)

(73) Assignee: COLGATE-PALMOLIVE COMPANY, New York, NY (US)

( * ) Notice: Subject to any disclaimer, the term of this patent is extended or adjusted under 35 U.S.C. 154(b) by 141 days.

(21) Appl. No.: 14/367,846

(22) PCT Filed: Dec. 21, 2011

(86) PCT No.: PCT/US2011/066568
§ 371 (c)(1),
(2), (4) Date: Jun. 20, 2014

(87) PCT Pub. No.: WO2013/095452
PCT Pub. Date: Jun. 27, 2013

(65) Prior Publication Data
US 2015/0327660 A1    Nov. 19, 2015

(51) Int. Cl.
*A46B 9/04* (2006.01)
*A46B 9/00* (2006.01)
(Continued)

(52) U.S. Cl.
CPC ............ *A46B 9/005* (2013.01); *A46B 15/0055* (2013.01); *A46B 9/04* (2013.01); *A61B 17/244* (2013.01)

(58) Field of Classification Search
CPC ..... A61B 17/244; A61B 17/24; A46B 15/022; A46B 15/005; A46B 15/0081; A46B 9/005; A46B 2200/1026; A46B 9/04
(Continued)

(56) References Cited

U.S. PATENT DOCUMENTS 5,810,856 A   9/1998  Tveras
5,980,542 A   11/1999 Saldivar
(Continued)

FOREIGN PATENT DOCUMENTS

CA      2394842       6/2001
DE    202005009026   10/2005
(Continued)

OTHER PUBLICATIONS

AU Patent Examination Report No. 1, dated Jul. 7, 2014 in corresponding AU Application No. 2011383564, filed May 28, 2014. AU.
(Continued)

*Primary Examiner* — Laura C Guidotti

(57) ABSTRACT

An oral care implement is provided, in one embodiment, with a plurality of spaced-apart tissue cleaning pads (400) radially arranged around a central axis (450) to form a grouping, each pad having an inner region (420, 430) close to the central axis and an outer region spaced away from the central axis, the inner region (420, 430) being raised relative to the outer region and having scraping surfaces along certain edge regions for improved cleaning of the soft tissue in an oral cavity Each pad further preferably includes one or more protrusions (920, 930) along an upper surface thereof.

18 Claims, 8 Drawing Sheets

(51) Int. Cl.
*A46B 15/00* (2006.01)
*A61B 17/24* (2006.01)

(58) Field of Classification Search
USPC .............. 15/110–111; D4/104, 108; 606/161
See application file for complete search history.

(56) References Cited

U.S. PATENT DOCUMENTS

| | | | |
|---|---|---|---|
| 6,004,334 | A | 12/1999 | Mythen |
| D537,165 | S | 2/2007 | Leite et al. |
| 7,174,596 | B2 * | 2/2007 | Fischer .................. A46B 3/06 15/110 |
| 7,607,189 | B2 * | 10/2009 | Moskovich ........ A46B 15/0055 15/110 |
| 7,908,699 | B2 | 3/2011 | Hohlbein et al. |
| 2004/0255416 | A1 | 12/2004 | Hohlbein |
| 2005/0166344 | A1 | 8/2005 | Hohlbein et al. |
| 2005/0210612 | A1 | 9/2005 | Hohlbein et al. |
| 2006/0195995 | A1 | 9/2006 | Moskovich et al. |
| 2006/0200925 | A1 * | 9/2006 | Moskovich .......... A46B 5/0029 15/167.1 |
| 2006/0222683 | A1 | 10/2006 | Mythen |
| 2008/0201884 | A1 | 8/2008 | Vazquez et al. |
| 2008/0208228 | A1 | 8/2008 | Mueller |
| 2009/0183324 | A1 | 7/2009 | Fischer et al. |
| 2009/0183331 | A1 | 7/2009 | Gross et al. |
| 2010/0043162 | A1 | 2/2010 | Zimmermann et al. |

FOREIGN PATENT DOCUMENTS

| | | |
|---|---|---|
| GB | 2451230 | 1/2009 |
| KR | 200455480 | 8/2009 |
| WO | WO98/08458 A2 | 3/1998 |
| WO | WO 2006/055572 A1 | 5/2006 |
| WO | WO 2008/076726 A1 | 6/2008 |
| WO | WO 2011/084115 A1 | 7/2011 |

OTHER PUBLICATIONS

Fresh Breath 400TC Toothbrush, www.injcanada.com/reach/en/products.asp, downloaded from the Internet, date unknown but prior to Dec. 21, 2011.
International Search Report and the Written Opinion issued in International Application PCT/US2011/66568 mailed Sep. 6, 2012. WO.
S535, Tongue Cleaner, www.chinabboss.com, downloaded from the Internet, date unknown but prior to Dec. 21, 2011.
S803, Tooth Brush, www.chinabboss.com downloaded from the Internet, date unknown but prior to Dec. 21, 2011.
Adult toothbrush 921, www.best-b2b.com, downloaded from the Internet, date unknown but prior to Dec. 21, 2011.

* cited by examiner

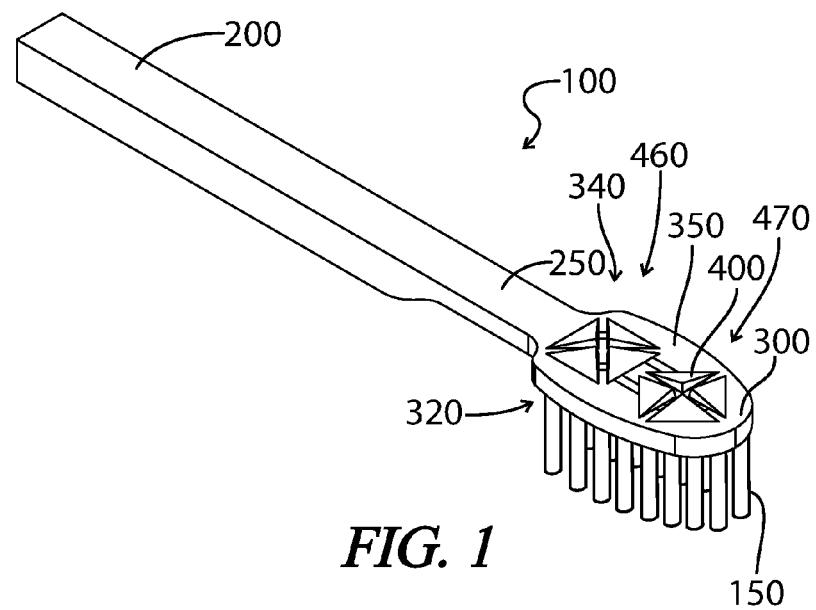

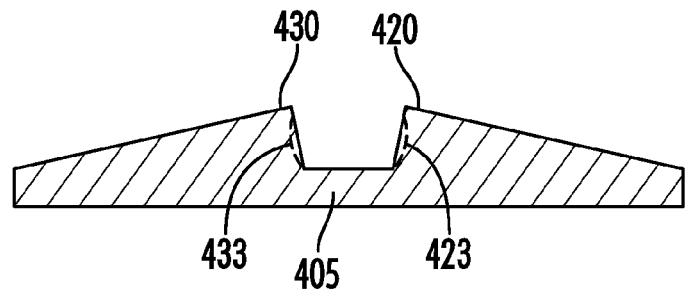
FIG. 3
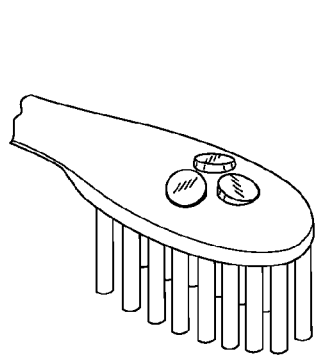 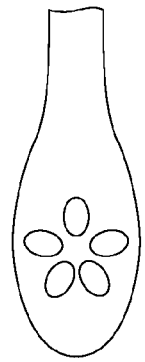 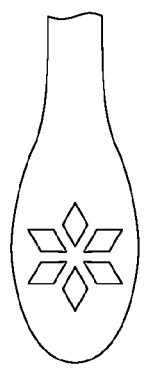
FIG. 4A    FIG. 4B    FIG. 4C

TISSUE CLEANER AND ORAL CARE IMPLEMENT

CROSS-REFERENCE TO RELATED APPLICATIONS

This application is a U.S. national stage application under 35 U.S.C. §371 of PCT Application No. PCT/US2011/066568, filed Dec. 21, 2011, the entirety of which is incorporated herein by reference.

FIELD OF THE INVENTION

The present invention relates to oral care implements generally, and more particularly to, in one embodiment, an oral care implement with, tissue cleaning pads.

BACKGROUND OF THE INVENTION

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can be lead bad breath or oral malodor.

Bladed tongue scrapers have been used in the past, but some users avoid the use of such blades because of lack of comfort on the tongue surface.

Hence, there is a need for an oral care implement with a tissue cleanser that provides effective removal of bacteria and other debris from the tongue and other soft tissue surfaces while maintaining comfort to the user.

BRIEF SUMMARY OF THE INVENTION

An oral care implement is provided, in one embodiment, with a head having a plurality of spaced-apart tissue cleaning pads radially arranged around a central axis to form a grouping, each pad having an inner region close to the central axis and an outer region spaced away from the central axis, the inner region being raised relative to the outer region and having scraping surfaces along certain edge regions for improved cleaning of the soft tissue in an oral cavity. The outer regions of the tissue cleaning pads are preferably flush with an outer surface of the head to provide comfort to a user as the oral care implement is drawn across a user's soft tissue surfaces. In another embodiment, each pad further preferably includes one or more protrusions along an upper surface thereof to provide additional cleaning surfaces. In another embodiment there is provided a bifurcated tissue cleaning pad having a bifurcated tooth cleaning element depending therefrom, the bifurcated tissue cleaning pad and the bifurcated tooth cleaning element provided with protrusions for enhanced cleaning of both soft tissue and tooth elements.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 illustrates one embodiment of an oral care implement.

FIG. 2 illustrates one embodiment of the rear of the head of the oral care implement of FIG. 1.

FIG. 3 is a cross-section taken along line 3-3 of FIG. 2.

FIGS. 4A-4C illustrate various embodiments of arrangements of tissue cleaner pads.

DETAILED DESCRIPTION OF THE INVENTION

Figure 5:
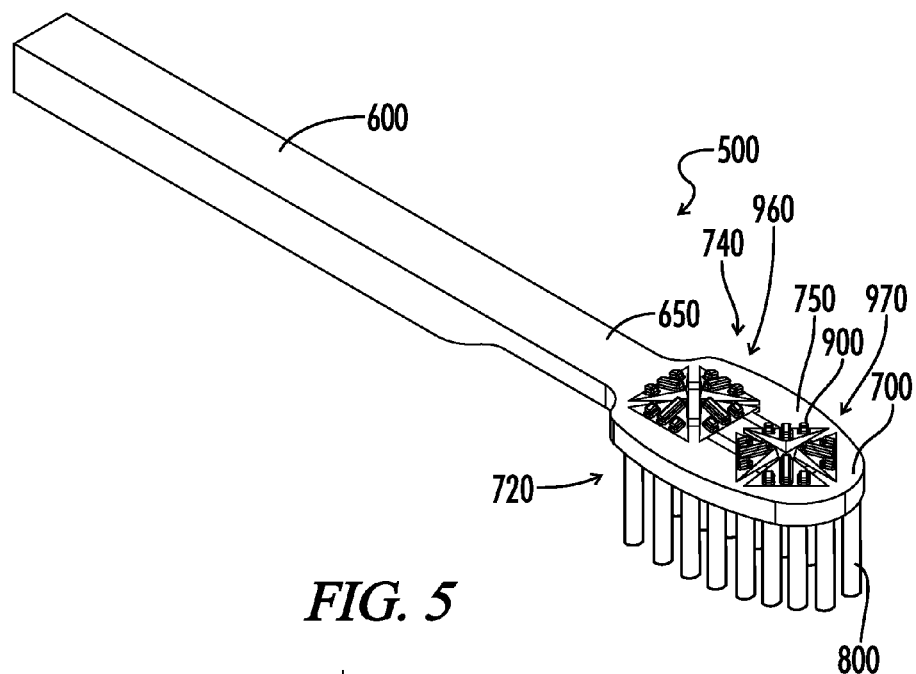
FIG. 5 illustrates a second embodiment of an oral care implement.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

FIGS. 1-3 illustrate one embodiment of an oral care implement 100 having a representative handle 200 for gripping by a user (not shown), a head 300 and a neck 250 defined therebetween. In the embodiment of FIG. 1, the oral care implement 100 is shown as a toothbrush where the head 300 has a first or front side 320 provided with tooth cleaning elements 150, and a second or rear side 340 having a rear surface 350 on which is provided one or more tissue-cleaning pads 400 for cleaning the soft tissue of the oral cavity such as the tongue and cheeks, for example. The rear side 340 and surface 350 is shown as relatively flat for purposes of describing certain features, although it will be appreciated that the head 300 and its respective surfaces may be curved or otherwise contoured as desired. The toothbrush 100 may be manual or powered or a combination of the same, and may be any shape, size, or material, while the cleaning elements 150 can be formed from any material composition and configuration as desired. For example, the cleaning elements 150 may comprise nylon bristles, elastomeric elements, rubber elements, and/or combinations of the same. The handle 200 is illustrated generically, it being understood that the handle 200 can be contoured, provided with gripping elements to enhance handling, and other features known in the art.

As shown in FIG. 2, each tissue-cleaning pad 400 further comprises an outer surface 410 having a plurality of edge regions 420, 430 that are at least partially raised from the rear surface 350 of the rear side 340 of the head 300, and at least one additional edge region 440 that is adjacent or substantially flush with the rear surface 350. The additional edge region 440 forms a smooth transition between the rear surface 350 of the head 300 and the tongue cleaning pads 400 that is comfortable to the user. The edge regions 420, 430 are elevated from the rear surface 350 by sloped walls 421, 431 that extend from a first area 422, 432 adjacent the rear surface 350 and converge toward an intersection 426 of the walls 421, 431. The intersection 426 of the walls 421, 431 may form a relatively sharp corner or it may comprise a smooth surface, or a combination of the same. Additional surface features or contours are possible. The edge regions 420, 430 intersect at an area that forms an apex 425 of the outer surface 410 where the apex 425 defines the highest elevation of the outer surface 410 relative to the rear surface 350 of the rear side 340 of the head 300.

Each wall 421, 431 functions as a scraping surface for scraping bacteria and the like from soft tissue that enters the spaces between the pads 400 and that contacts the walls 421, 431 of each pad as the oral care implement 100 is drawn across the various surfaces of soft tissue in the oral cavity. One or each wall 421, 431 may optionally further comprise a recessed central portion 423, 433 (FIG. 3) that is preferably slightly inwardly curved to provide an additional scooping action in addition to a scraping action, wherein the edge regions 420, 430 slightly overhang the recessed central portions 423, 433. The overall scraping action experienced by the pad walls 421, 431 is mitigated by the smoothness of the transition between the additional edge regions 440 and the head surface 350 provided around the outer edge of each pad 400. Thus, a user will obtain the cleaning benefit of the scraping walls 421, 431 near the intersections of the pads without being subject to an aggressive pad topography formed by scraping surfaces along all of the edge regions 420, 430, 440. The tissue cleaning pads 400 are preferably composed of a soft and pliable elastomeric material for comfortable cleaning and effective removal of bacteria and debris disposed on the surface of the tongue, other soft tissue in the mouth and even along the lips. The tissue cleaner pads 400 also provide effective massaging, stimulation and removal of bacteria, debris and epithelial cells from the surfaces of the tongue, cheeks, gums or lips. The pads preferably have a Shore hardness of 8 to 35 Shore A.

In the embodiment of FIG. 1, there are a plurality of spaced-apart (bifurcated), wedge-shaped tissue cleaning pads 400 radially arranged around a central axis 450 to form a plurality of groupings 460, 470. While a plurality of groupings 460, 470 are shown, it will be appreciated that only one grouping (FIG. 4A) may be used, or more than two groupings (not shown) if desired. Other arrangements are possible. In addition, while wedge-shaped pads 400 are shown in the embodiment of FIGS. 1-3, for example, it will be appreciated that other shapes and configurations are possible, such as, but not limited to, circular (FIG. 4A), oval (FIG. 4B), diamond-shaped (FIG. 4C), and the like.

Returning to FIGS. 1-3, the pads 400 in each grouping are interconnected by bridges 405, while an additional bridge 465 spans between one pad 400 from each grouping 460, 470 to interconnect the groupings 460, 470 together. While a bridge 465 is defined between groupings 460, 470, each grouping may exist independent of the other, in which case a bridge may not be provided between groupings. The bridges 465, 460, 470 positionally align the pads 400 relative to each other and increase the structural integrity of the pad groupings during the manufacturing process. The bridges 405, 465 may be flush with the rear surface 350 of the head 300 as shown, or they may be embedded within the head (not shown) so that only the pads 400 are visible, or they may be situated on top of the rear surface 350 of the head 300. In addition, the bridges 405, 465 may be located toward the centers of the pads 400 as shown, or they array be situated in different locations relative to the pads 400 as desired. A variety of different aesthetic effects may also be created by varying the relative positions of the pads, or of the bridges relative to the pads, and by varying the relative positions of each grouping of pads.

Figure 6A:
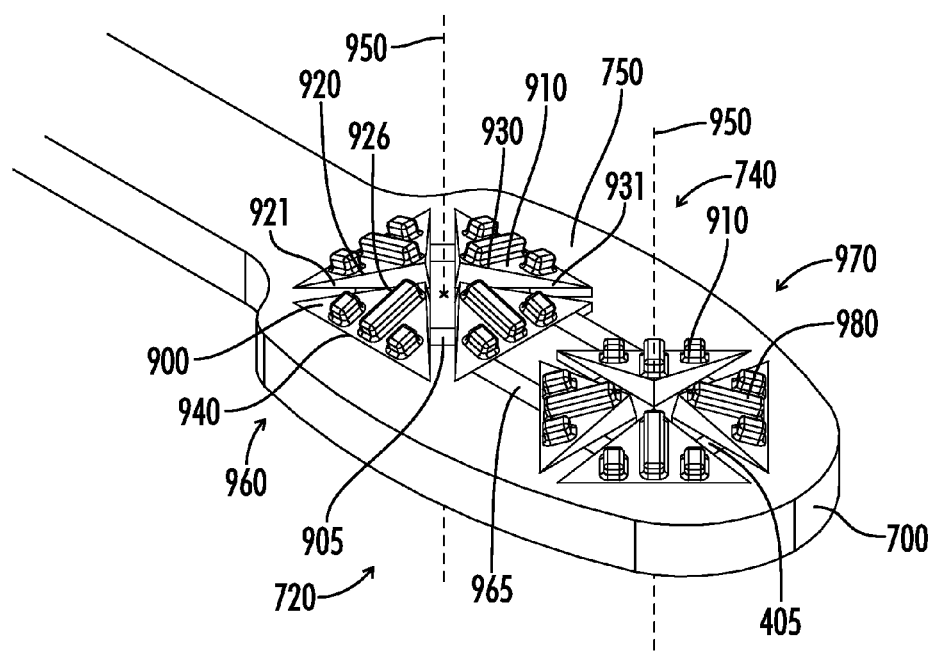
FIG. 6A illustrates one embodiment of the rear of the head of the oral care implement of FIG. 5.
Figure 6B:
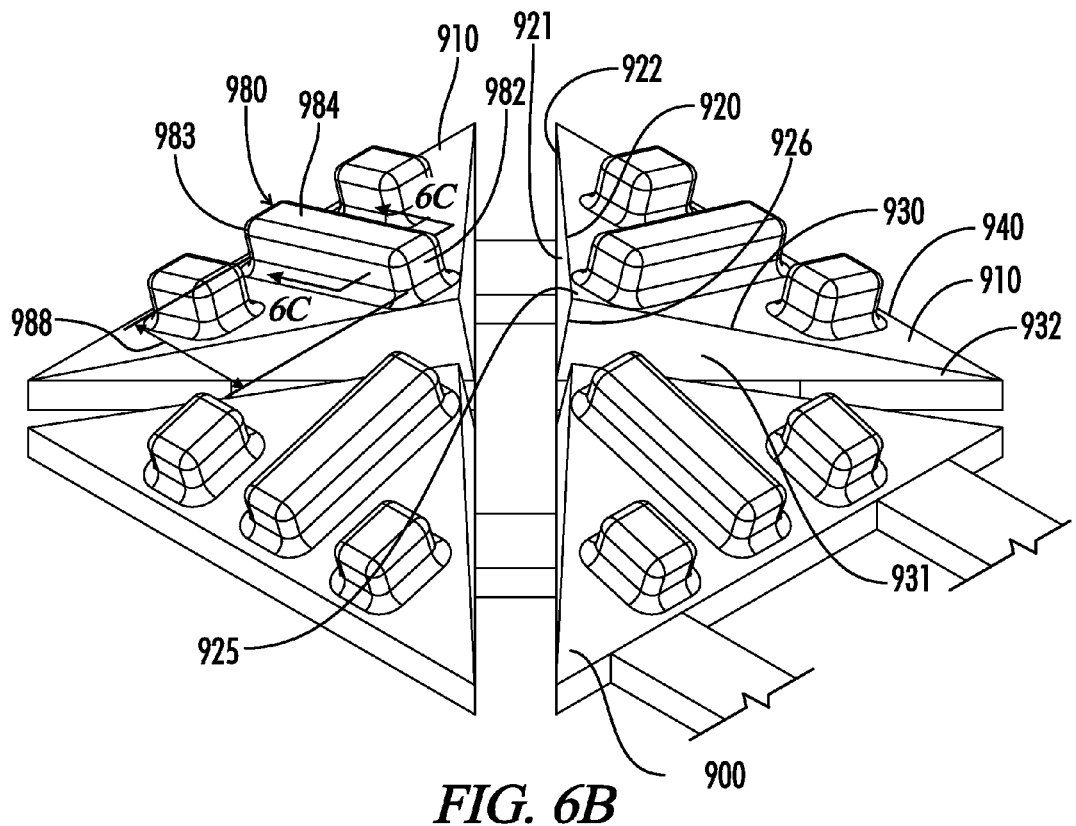
FIG. 6B illustrates a close-up view of an aspect of the rear of the head.
Figure 6C:
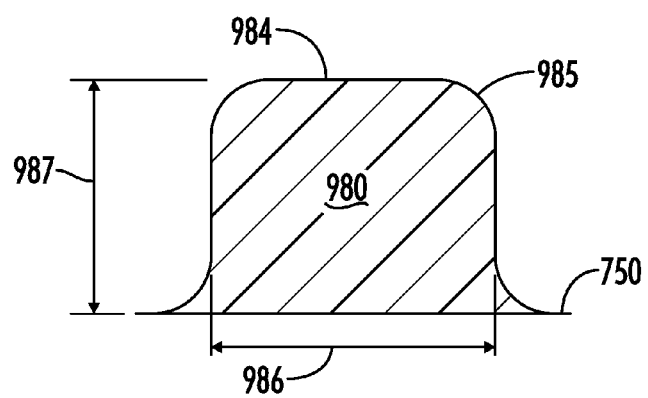
FIG. 6C illustrates a cross-section taken along line 6C-6C of FIG. 6B.

FIGS. 5-6C illustrate another embodiment of an oral care implement 500 having a handle 600 for gripping by a user (not shown), a head 700 and a neck 650 defined therebetween, the head 700 having a first or front side 720 provided with tooth cleaning elements 800, and a second or rear side 740 having a rear surface 750 on which is provided one or more tissue-cleaning pads 900 enhanced with protrusions 980 for cleaning the soft tissue of the oral cavity such as the tongue and cheeks, for example. The rear side 740 and surface 750 is shown as relatively flat for purposes of describing certain features, although it will be appreciated that the head 700 and its respective surfaces may be curved or otherwise contoured as desired. The toothbrush 500 may be manual or powered or a combination of the same, and may be any shape, size, or material, while the cleaning elements 800 can be formed from any material composition and configuration as desired. The handle 600 is illustrated generically, it being understood that the handle 600 can be contoured, provided with gripping elements to enhance handling, and other features known in the art.

Figure 8:
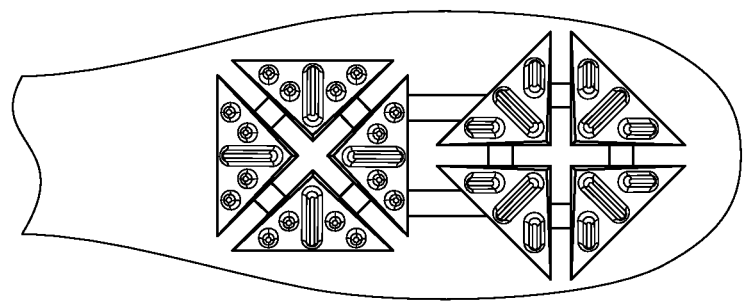

As shown in FIGS. 6A-6C, each tissue-cleaning pad 900 further comprises an outer surface 910 having a plurality of edge regions 920, 930 that are at least partially raised from the rear surface 750 of the rear side 740 of the head 700, and at least one additional edge region 940 that is adjacent or substantially flush with the rear surface 750. The pads 900 are interconnected by bridges 905 and are radially arranged around a central soda 950 to form groupings 960, 970 that are interconnected by a bridge 965. The edge regions 920, 930 are elevated from the rear surface 750 by sloped walls 921, 931 that converge toward an intersection 926 and that form scraping surfaces as previously described. The outer surface 910 of each pad 900 further comprises a plurality of bar-shaped protrusions 980 that are arranged along the outer surface 910 of the pad 900 and that are directionally oriented toward the central axis 950. The bar-shaped protrusions 980 generally comprise a proximal end 982, a distal end 983, and an upper surface 984. The bar-shaped protrusions have a thickness 986 (FIG. 6C) and extend a height 987 from the rear surface 750 of the head 700. Additionally, the bar-shaped protrusions 980 extend for a length 988 (FIG. 6A) along the outer surface 910 of the pad 900 and are directionally oriented from the edge region 940 to the edge regions 920, 930 toward the central axis 950. The length 988 of each bar-shaped protrusion 980 may vary from an adjacent bar-shaped protrusion by virtue of the changing geometry of the outer surface 910 of the pad 900. In the illustrated embodiment, the bar-shaped protrusion with the greatest length is aligned with the intersection 926 of the walls 921, 931 and the apex 925 of the outer surface 910. This provides at least one bar-shaped protrusion at the highest elevation for additional reach between the papillae of the tongue and other soft tissue during use of the toothbrush 500. Preferably, the height 987 of the bar-shaped protrusions is between 0.5 mm and 1.25 mm as measured from the rear surface 750 of the head 700. The upper surface 984 of each of the bar-shaped protrusions 980 has curved outer edges 985 so as to minimize sharp edges at the point of contact with the soft tissue. In one embodiment, the bar shaped protrusions 980 are arranged in a substantially parallel configuration relative to each other. However, other arrangements are possible including non-parallel configurations wherein the proximal end 982 of each bar-shaped protrusion 980 is toward the apex 925, while the distal end 983 of each bar-shaped protrusion fans out in alignment with the sloped walls 921, 931 (see, for example, FIG. 8).

Figure 7:
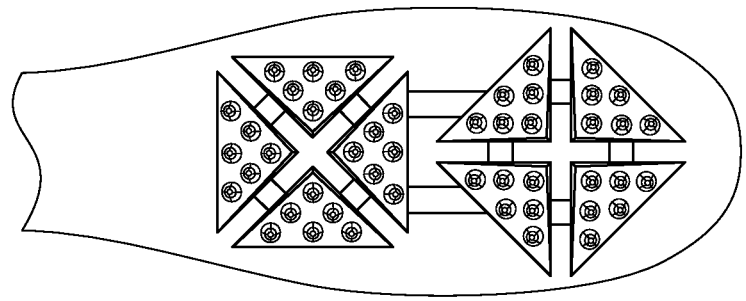
FIGS. 7-9 illustrate various embodiments of arrangements of tissue cleaner pads.
Figure 9:
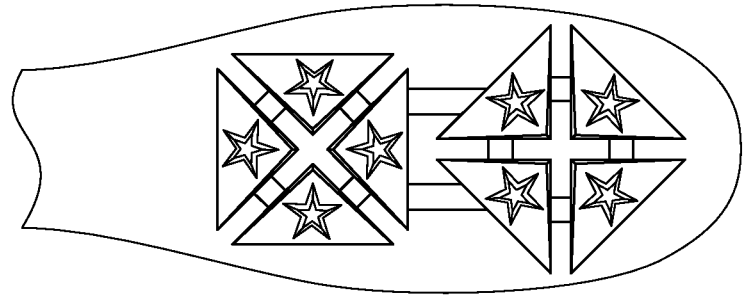

The bar-shaped protrusions 980 are preferably made of the same material as the pad 900. In some embodiments, the bar-shaped protrusions 980 and the pad 900 are made of a thermoplastic elastomer. In other embodiments, however, the bar-shaped protrusions 980 and the pad 900 are each made of a different material. For example, the bar-shaped protrusions could be a plastic that is the same material as the head 700 and molded together with the head in a first step in the molding process. The pad 900 could be made of a second softer material, preferably a thermoplastic elastomer having a Shore A hardness in the range of 8 to 35 Shore A. The softer pad 900 would then be injection molded over the head 700 such that the bar-shaped protrusions extend from the outer surface of the head and through the pad 900 so that the outer surface of the bar-shaped protrusion 980 is exposed through the pad 900. Alternatively, the pad 900 could be injection molded over the bar-shaped protrusion 980 so that the bar-shaped protrusion 980 is made of the inner, harder plastic, which is covered by an outer layer of the softer material from which the pad 900 is made. In one embodiment, the bar-shaped protrusion is made of polypropylene and the pad 900 is made of thermoplastic elastomer having a Shore A hardness in the range of 8 to 35 Shore A. While bar protrusions 980 are shown, it will be appreciated that other configurations are possible, including, but not limited to, bumps as shown for example in FIG. 7, a combination of bumps and bars as shown for example in FIG. 8, or single protrusions such as the single star-shaped protrusions shown in FIG. 9. Other configurations are possible. The protrusions 980 provide the pads 900 with additional scraping surfaces that act in conjunction with the sloped walls 921, 931 for cleaning bacteria from soft tissue. However, even though the protrusions 980 provider, an enhanced sensory experience for the user, the additional edge regions 940 maintain a smooth transition between the rear surface 750 of the head 700 and the pads 900 to minimize the aggressiveness of the outwardly oriented edges of the pads 900.

Figure 10:
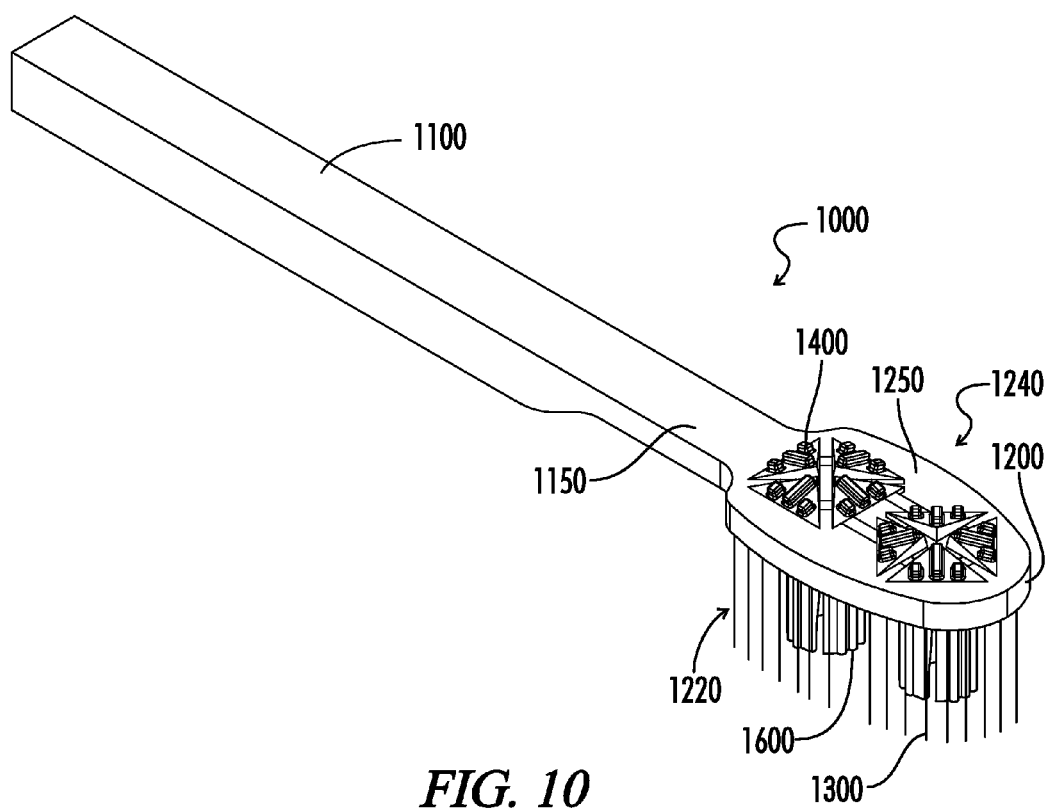
FIG. 10 illustrates a third embodiment of an oral care implement.
Figure 11A:
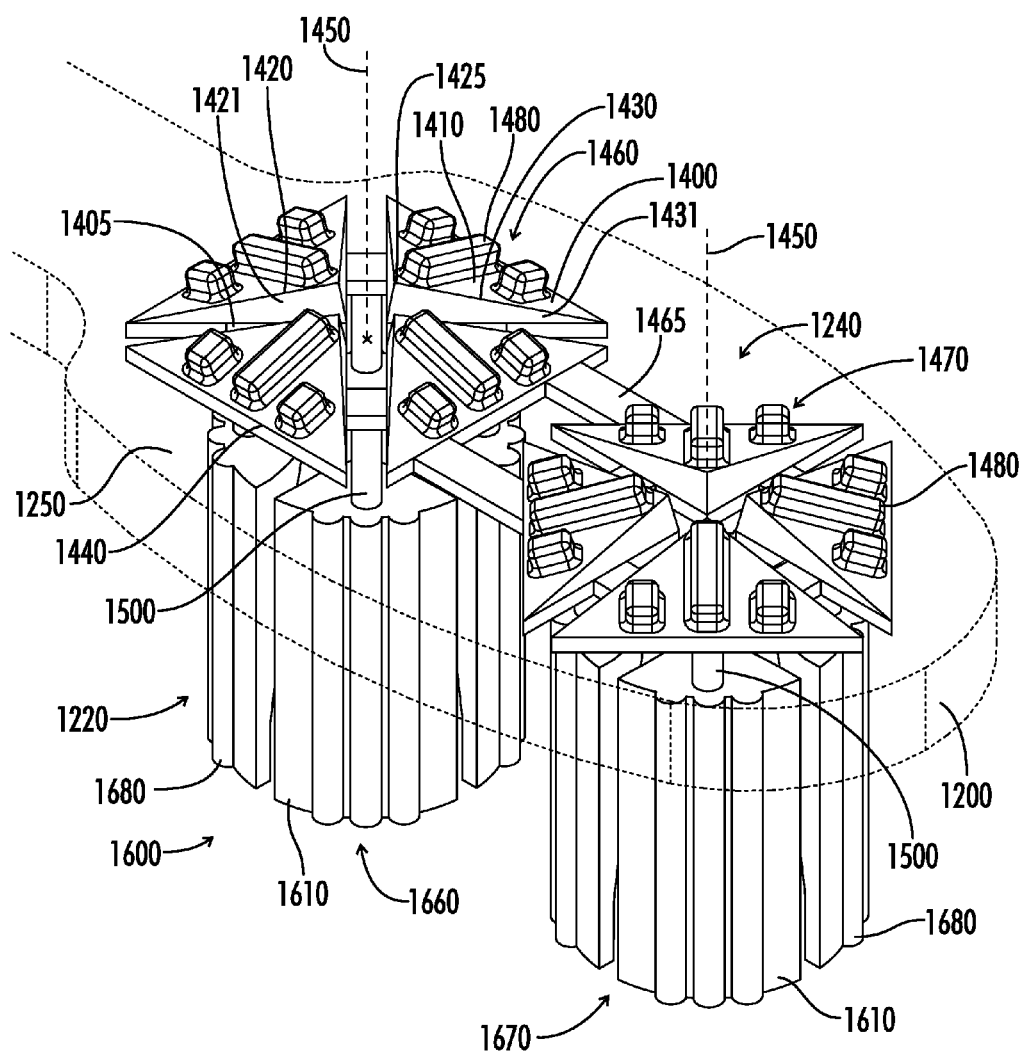
FIG. 11A illustrates one embodiment of the head of the oral care implement of FIG. 10.
Figure 11B:
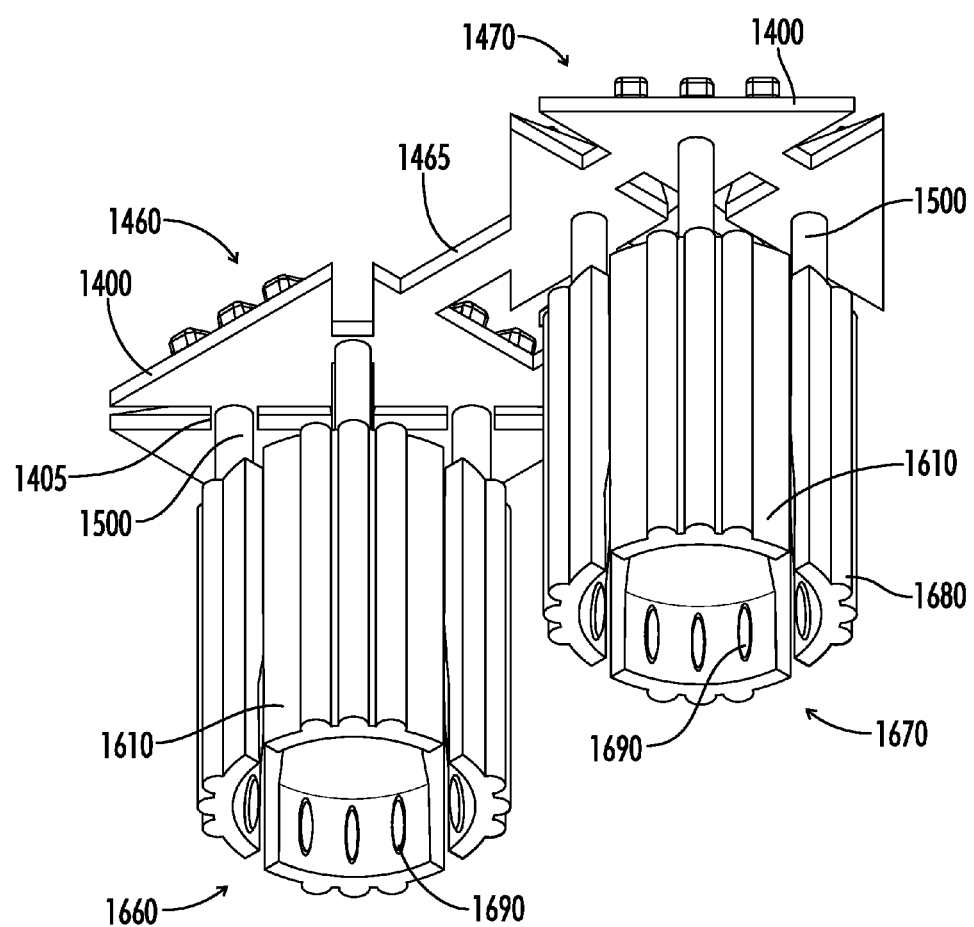
FIG. 11B illustrates one embodiment of the tissue cleaning pads and tooth cleaning elements of the oral care implement of FIG. 10.

FIGS. 10-11B illustrate yet another embodiment of an oral care implement 1000 having a handle 1100 for gripping by a user (not shown), a head 1200 and a neck 1150 defined therebetween. The head 1200 has a first or front side 1220 provided with tooth cleaning elements 1300, and a second or rear side 1240 having a rear surface 1250 on which is provided one or more tissue-cleaning pads 1400. The rear side 1240 and surface 1250 is shown as relatively flat for purposes of describing certain features, although it will be appreciated that the head 1200 and its respective surfaces may be curved or otherwise contoured as desired. The tissue cleaning pads 1400 have associated tooth cleaning elements 1600 depending from connecting members 1500 that extend through the head 1200, the tooth cleaning elements 1600 preferably being formed from the same material as the tissue cleaning pads 1400 for ease of manufacturing. The tooth cleaning elements 1300 shown in FIG. 10 are omitted from FIGS. 11A-11B to better illustrate the tooth cleaning elements 1600. The handle 1100 is illustrated generically, it being understood that the handle 1100 can be contoured, provided with gripping elements to enhance handling, and other features known in the art.

As shown in FIGS. 11A-11B, each tissue-cleaning pad 1400 further comprises an outer surface 1410 having a plurality of edge regions 1420, 1430 that are at least partially raised from the rear surface 1250 of the rear side 1240 of the head 1200, and at least one additional edge region 1440 that is adjacent or substantially flush with the rear surface 1250. The pads 1400 are preferably interconnected by bridges 1405 and are radially arranged around a central axis 1450 to form groupings 1460, 1470 that are interconnected by a bridge 1465. The edge regions 1420, 1430 intersect along an area 1425 that is near the central axis 1450 and are elevated from the rear surface 1250 by sloped walls 1421, 1431. The outer surface 1410 of each pad 1400 further comprises a plurality of bar-shaped protrusions 1480 that are arranged in a substantially parallel configuration along the outer surface 1410 of the pad 1400 and that are directionally oriented toward the central axis 1450. While bar protrusions are shown, it will be appreciated that other configurations are possible.

In the embodiment of FIGS. 11A-11B, each grouping 1460, 1470 describes a bifurcated tissue-cleaning pad defined by a plurality of spaced-apart wedge-shaped pads 1400 radially arranged around a central axis 1450 and connected by bridges 1405, 1465, each pad having one or more protrusions 1480, an inner region 1425 close to the central axis 1450 and an outer region 1440 spaced away from the central axis 1450, the inner region 1425 being raised relative to the outer region 1440. The tooth cleaning elements 1600 are similarly bifurcated into a plurality of individual tooth cleaning elements 1610 that each extend downward through the head 1200 (FIG. 11A) relative to the pads 1400, where first and second groupings 1660, 1670 of tooth cleaning elements 1610 extend from the first and second groupings 1460, 1470 of pads 1400. The bridge 1465 between the pad groupings 1460, 1470 links the cleaning element groupings 1660, 1670 together to form a unified arrangement of tissue cleaning pads 1400 and tooth, cleaning elements 1610, where the tissue cleaning pads are arranged in a first plane and the tooth cleaning elements 1610 are arranged in a second plane that is substantially perpendicular to the first plane. The unified arrangement allows for the tissue cleaning pads 1400 to be injection molded with the tooth cleaning elements 1610 in a single injection-molding step during the manufacturing process. This creates an efficiency in the process which allows for faster manufacturing while at the same time increasing the structural integrity of the tissue cleaning pads 1400 and the tooth cleaning elements 1610.

In one grouping 1460, the connecting members 1500 extend from the bridges 1405 interconnecting the pads 1400, while in another grouping 1470 the connecting members 1500 extend from the pads 1400, her connection scenarios are possible. Each cleaning element 1610 further comprises outer protrusions 1680 extending along a plane that is substantially perpendicular to the plane of the pad protrusions 1480, and inner protrusions 1690 defined within the interior of a grouping 1660, 1670 of elements 1610, the protrusions 1680, 1690 providing scraping surfaces upon impact with a user's teeth and soft tissue if desired. In one grouping 1460, 1660 the protrusions 1480, 1680 are directionally aligned, while in the other grouping 1470, 1670 the protrusions are not aligned.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:

1. An oral care implement comprising:
   a head having a first side and a second side that is opposite the first side;
   a plurality of spaced-apart tissue cleaning pads positioned on the first side of the head and radially arranged around a central axis to form a grouping, each tissue cleaning pad further comprising a top surface having a perimeter comprising:
      a first edge at least partially raised from the first side of the head;
      a second edge at least partially raised from the first side of the head;
      a third edge that is flush with the first side of the head; and
   bridges connecting the tissue cleaning pads.

2. The oral care implement of claim 1, wherein the first and second edges of the top surface of each of the tissue cleaning pads converge and intersect to form a first corner of the perimeter of the top surface and the first corner of the perimeter of the top surface is closer to the central axis than the third edge of the perimeter of the top surface.

3. The oral care implement of claim 1, further comprising a second plurality of spaced-apart tissue cleaning pads positioned on the first side of the head and radially arranged around a second central axis to form a second grouping.

4. The oral care implement of claim 1, further comprising a plurality of protrusions extending from the top surface of each of the plurality of tissue cleaning pads.

5. The oral care implement of claim 1, wherein the top surface of each of the tissue cleaning pads slopes downward toward the first side of the head with increasing distance from the central axis.

6. An oral care implement comprising:
   a head having a first side and a second side that is opposite the first side;
   a plurality of spaced-apart tissue cleaning pads positioned on the first side of the head and radially arranged around a central axis to form a grouping, each tissue cleaning pad further comprising a top surface having a perimeter comprising:
      a first edge at least partially raised from the first side of the head;
      a second edge at least partially raised from the first side of the head;
      a third edge that is flush with the first side of the head; and
   a plurality of groupings of tissue cleaning pads connected by a bridge between one tissue cleaning pad in each grouping.

7. An oral care implement comprising:
   a head having a first side and a second side that is opposite the first side;
   a plurality of spaced-apart tissue cleaning pads positioned on the first side of the head and radially arranged around a central axis to form a grouping, each tissue cleaning pad further comprising a top surface having a perimeter comprising:
      a first edge at least partially raised from the first side of the head;
      a second edge at least partially raised from the first side of the head;
      a third edge that is flush with the first side of the head;
   a second plurality of spaced-apart tissue cleaning pads positioned on the first side of the head and radially arranged around a second central axis to form a second grouping; and
   a bridge connecting one of the tissue cleaning pads in the grouping with one of the tissue cleaning pads in the second grouping.

8. The oral care implement of claim 7, wherein the central axis and the second central axis do not intersect or coincide.

9. An oral care implement comprising:
   a head having a first side and a second side and a plurality of spaced apart tissue cleaning pads positioned on the first side of the head and radially arranged around a central axis to form a grouping, each tissue cleaning pad further comprising a top surface having a perimeter comprising:
      a first edge at least partially raised from the first side of the head; and
      a second edge at least partially raised from the first side of the head;
   wherein the first and second edges converge and intersect to form a first corner of the perimeter of the top surface;
   wherein the first corner of the perimeter of the top surface of each tissue cleaning pad in the grouping faces the central axis without intersecting the central axis; and
   wherein the first and second edges of the top surface of each tissue cleaning pad intersect the first side of the head at an acute angle.

10. The oral care implement of claim 9, the top surface of each of the tissue cleaning pads further comprising at least one protrusion.

11. The oral care implement of claim 9, wherein the perimeter of the top surface of each of the tissue cleaning pads further comprises a third edge, the third edge being flush with the first side of the head.

12. An oral care implement comprising:
a head having a first side and a second side and a plurality of spaced apart tissue cleaning pads positioned on the first side of the head and radially arranged around a central axis to form a grouping, each tissue cleaning pad further comprising a top surface having a perimeter comprising:
  a first edge at least partially raised from the first side of the head; and
  a second edge at least partially raised from the first side of the head;
wherein the first and second edges converge and intersect to form a first corner of the perimeter of the top surface;
wherein the first corner of the perimeter of the top surface of each tissue cleaning pad in the grouping faces the central axis without intersecting the central axis;
wherein each of the tissue cleaning pads further comprises:
  a first side wall extending between the first side of the head and the first edge of the perimeter; and
  a second side wall extending between the first side of the head and the second edge of the perimeter; and
wherein the first side wall and the second side wall converge and intersect to form a side wall edge that faces the central axis.

13. The oral care implement of claim 12, wherein the perimeter of the top surface of each of the tissue cleaning pads further comprises a third edge that is flush with the first side of the head, the first corner of the perimeter of the top surface is closer to the central axis than the third edge of the perimeter of the top surface.

14. The oral care implement of claim 13, wherein the top surface of each of the tissue cleaning pads slopes downward toward the first side of the head from the first corner to the third edge.

15. A tongue-cleaning pad comprising:
a first plurality of spaced-apart wedge-shaped elements radially arranged around a first central axis and connected by a first plurality of bridges, each of the first plurality of spaced-apart wedge-shaped elements having one or more protrusions;
a second plurality of spaced-apart wedge-shaped elements radially arranged around a second central axis and connected by a second plurality of bridges, each of the second plurality of spaced-apart wedge-shaped elements having one or more protrusions; and
a third bridge connecting one of the first plurality of spaced-apart wedge-shaped elements to one of the second plurality of spaced-apart wedge-shaped elements.

16. The tongue-cleaning pad of claim 15, wherein each of the wedge-shaped elements of the first and second plurality of wedge-shaped elements have a top surface having a perimeter comprising:
  a first edge at least partially raised from the first side of the head;
  a second edge at least partially raised from the first side of the head; and
  a third edge that is flush with the first side of the head;
wherein the first plurality of bridges, the second plurality of bridges, and the third bridge are all flush with the first side of the head.

17. The tongue-cleaning pad of claim 16, wherein the first plurality of bridges extend between raised side walls of adjacent ones of the first plurality of wedge-shaped elements and the second plurality of bridges extend between raised side walls of adjacent ones of the second plurality of wedge-shaped elements.

18. The tongue-cleaning pad of claim 17, wherein the third bridge connects the third edge of one of the wedge-shaped elements of the first plurality of wedge-shaped elements to the third edge of one of the wedge-shaped elements of the second plurality of wedge-shaped elements.

* * * * *